(12) United States Patent
Appel et al.

(10) Patent No.: US 8,609,883 B2
(45) Date of Patent: Dec. 17, 2013

(54) CONTINUOUS METHOD FOR PRODUCING ACYL PEROXIDES

(75) Inventors: Hans Appel, Penzberg (DE); Wilfried Meichelböck, Kralling (DE); Josef Helmut Weinmaier, Mühldorf (DE); Helmut Zellner, Hörbach (DE)

(73) Assignee: United Initiators GmbH & Co. KG, Pullach (DE)

( * ) Notice: Subject to any disclaimer, the term of this patent is extended or adjusted under 35 U.S.C. 154(b) by 853 days.

(21) Appl. No.: 12/309,160

(22) PCT Filed: Jun. 18, 2007

(86) PCT No.: PCT/EP2007/056006
§ 371 (c)(1),
(2), (4) Date: Oct. 5, 2009

(87) PCT Pub. No.: WO2008/006666
PCT Pub. Date: Jan. 17, 2008

(65) Prior Publication Data
US 2010/0036152 A1    Feb. 11, 2010

(30) Foreign Application Priority Data
Jul. 12, 2006  (DE) .......................... 10 2006 032 165

(51) Int. Cl.
*C07C 69/76* (2006.01)
(52) U.S. Cl.
USPC ....................................................... 560/103
(58) Field of Classification Search
None
See application file for complete search history.

(56) References Cited

U.S. PATENT DOCUMENTS

| | | | |
|---|---|---|---|
| 3,367,951 A | | 2/1968 | Nielsen et al. |
| 3,849,468 A | * | 11/1974 | Busseret ........................ 558/269 |
| 3,950,375 A | | 4/1976 | McKee et al. |
| 4,075,236 A | | 2/1978 | Wagle et al. |
| 5,831,131 A | | 11/1998 | Krespan et al. |
| 6,303,825 B1 | * | 10/2001 | Gerlich et al. ................. 568/385 |
| 6,307,112 B1 | | 10/2001 | Weber et al. |
| 2004/0249097 A1 | * | 12/2004 | Cozens et al. ............. 526/230.5 |
| 2009/0043122 A1 | | 2/2009 | Azzawi et al. |

FOREIGN PATENT DOCUMENTS

| | | |
|---|---|---|
| DE | 2256255 | 5/1973 |
| DE | 128663 | * 11/1977 |

(Continued)

OTHER PUBLICATIONS

English translation of DD 128663, Rossner et al. (1977).*

(Continued)

*Primary Examiner* — Johann R Richter
*Assistant Examiner* — Jennifer C Sawyer
(74) *Attorney, Agent, or Firm* — Fulbirght & Jaworski LLP

(57) ABSTRACT

The invention relates to a continuous method for producing acyl peroxides. According to said method, an acyl chloride, carboxylic acid anhydride or chloroformate is reacted with an organic hydroperoxide or hydrogen peroxide in at least two mixed reaction zones that are connected in series, the acyl compound, the peroxy compound and an aqueous solution of a base being supplied to the first reaction zone. The first reaction zone comprises a cycle for the two-phase reaction mixture via a heat exchanger in which the reaction mixture is cooled. The method allows the reaction to be carried out reliably and with high space-time yields.

13 Claims, 1 Drawing Sheet

(56) References Cited

FOREIGN PATENT DOCUMENTS

| | | |
|---|---|---|
| DE | 19911024 A1 | 9/2000 |
| JP | 52-087119 A | 7/1977 |
| JP | 53-044514 A | 4/1978 |
| JP | 57-005226 B | 1/1982 |
| JP | 11-511464 A | 10/1999 |
| WO | WO-2007/042313 A | 4/2007 |

OTHER PUBLICATIONS

John C. Middleton, et al., Ulmann's Encyclopedia, Stirred-Tank and Loop Reactors, Jun. 15, 2005, Wiley-Vch Verlag GmbH & Co KGaA (XP002449394), pp. 1-14.

* cited by examiner

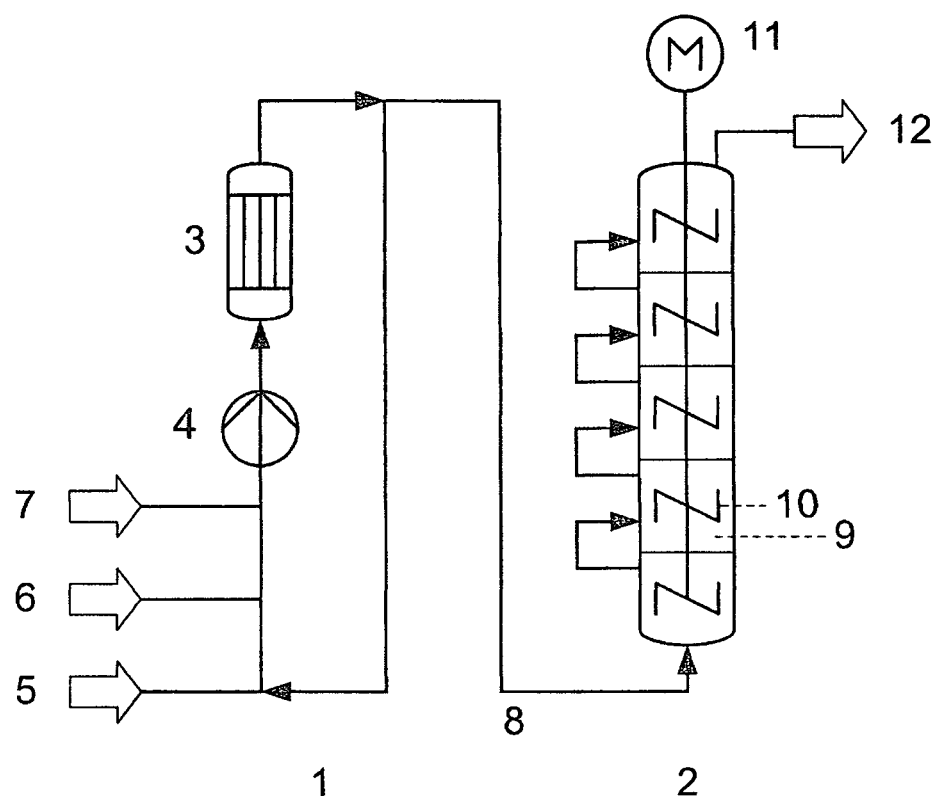

CONTINUOUS METHOD FOR PRODUCING ACYL PEROXIDES

RELATED APPLICATIONS

This application is a §371 of PCT/EP2007/056006 filed Jun. 18, 2007, which claims priority from German Patent Application No: 10 2006 032 165.0 filed Jul. 12, 2006.

The invention is directed to a process for preparing acyl peroxides, which can be performed safely and with high space-time yields.

Acyl peroxides are typically prepared by reacting an acyl compound from the group of the acid chlorides, carboxylic anhydrides and chloroformates with a peroxygen compound from the group of the organic hydro-peroxides and hydrogen peroxide. The reaction is effected with addition of an aqueous solution of an alkali metal hydroxide or alkaline earth metal hydroxide in order to bind the acid released in the reaction of the acyl compound with the peroxygen compound. The reaction is effected in a biphasic reaction mixture and proceeds exothermically.

Acyl peroxides find industrial use as initiators for polymerization reactions, for crosslinking reactions for polymers and for the curing of unsaturated polyester resins. These applications are based on the decomposition of the acyl peroxides at the labile oxygen-oxygen bond to free radicals. Depending on the chemical structure of the peroxide, this decomposition proceeds at different temperatures and with a different rate. The heat released in the decomposition leads, in the case of inadequate heat removal, to self-acceleration of the decomposition procedure, which becomes a usually violent decomposition and in the worst case can lead to explosion.

For the safe preparation of acyl peroxides, processes which can be performed below the self-accelerating decomposition temperature (SADT) and which proceed with a low reactor volume and high space-time yield are required, so that only a small amount of acyl peroxide is present in the reactor in each case.

U.S. Pat. No. 3,849,468 discloses a continuous process for preparing acyl peroxides in a loop reactor. In this process, only the aqueous phase of the reaction mixture is circulated, since the organic phase is removed with the product after each pass through the reaction column and only the aqueous phase is recycled into the reaction column. The process requires the use of a solvent and allows for space-time yields in the range of 0.1 to 0.47 mol/l·h, as is evident from the examples.

U.S. Pat. No. 4,075,236 discloses a process improved over the latter, in which the reaction is effected continuously in two stirred tanks connected in series, the feedstocks being fed to the first stirred tank. The process allows for a reaction without solvent with space-time yields in the range of 1.3 to 2.0 mol/l·h.

DD 128 663 discloses a process analogous to U.S. Pat. No. 4,075,236, in which the reaction is effected continuously in 4 to 7 stirred tanks connected in series. At reaction temperatures of 40 to 95° C., which are above the self-accelerating decomposition temperature (SADT), space-time yields in the range of 16 to 74 mol/l·h are achieved.

EP 847 387 describes a process for continuously preparing acyl peroxides in a flow apparatus which comprises a mixed reactor and a downstream connecting line, wherein at least 10% of the conversion is effected in the downstream connecting line. In the mixing reactor, an intensive mixer in the form of a jet mixer, ultrasound generator, static mixer or rotor/stator mixer is used. The process described cannot reliably be scaled up to an industrial scale, since, with at least 10% of the conversion in the downstream connecting line, the required heat removal can be ensured only at the small line cross sections of a laboratory apparatus.

US 2004/0249097 describes a process for preparing emulsions of acyl peroxides which have droplet sizes of the acyl peroxide of less than 10 µm. In the process, an acyl compound and a peroxygen compound are reacted in the presence of a dispersant. In one embodiment of the process, the reaction is effected in an in-line homogenizer which can be operated with circulation in order to achieve a plurality of passages for the homogenization. However, it is possible with this process to obtain only emulsions of acyl peroxides and not acyl peroxides in pure form.

It has now been found that the object of safe preparation of acyl peroxides at low temperatures and high space-time yields can be achieved by the process according to the invention, which also enables the preparation of acyl peroxides in pure form without the use of a solvent.

The invention provides a continuous process for preparing acyl peroxides by reacting an acyl compound from the group of the acid chlorides, carboxylic anhydrides and chloroformates with a peroxygen compound from the group of the organic hydroperoxides and hydrogen peroxide, the reaction being effected in at least two mixed reaction zones connected in series and the acyl compound, the peroxygen compound and an aqueous solution of a base being fed to the first reaction zone, wherein the process is characterized in that the first reaction zone comprises circulation of the biphasic reaction mixture through a heat exchanger in which the reaction mixture is cooled.

In the process according to the invention, an acyl compound and a peroxygen compound are reacted in at least two mixed reaction zones connected in series. Mixed reaction zones in the context of the invention are reaction zones in which the mixing ensures a substantially uniform composition of the reaction mixture within the reaction zone. Between the reaction zones connected in series, in contrast, no back-mixing takes place, i.e. no reaction mixture is recycled from a downstream reaction zone into an upstream reaction zone. The mixed reaction zones can be designed as separate reactors. Alternatively, it is also possible for two or more mixed reaction zones to be designed in a common apparatus. Suitable embodiments for mixed reaction zones are, for example, stirred tank reactors or loop reactors. The process according to the invention preferably comprises 2 to 8 mixed reaction zones connected in series.

In the process according to the invention, the acyl compound and the peroxygen compound are fed to the first reaction zone. Also fed to the first reaction zone is an aqueous solution of a base. The bases used may be water-soluble metal hydroxides, water-soluble quaternary ammonium hydroxides or water-soluble tertiary amines. Preferably, an alkali metal hydroxide or an alkaline earth metal hydroxide is used as the base, more preferably sodium hydroxide or potassium hydroxide. The peroxygen compound and the aqueous solution of the base can be mixed before they are fed to the first reaction zone. Alternatively, they can also be fed separately to the first reaction zone. Acyl compound and peroxygen compound can be fed continuously or intermittently, preference being given to a continuous feed. The aqueous solution of the base can, as desired, also be fed continuously or intermittently. In a preferred embodiment, the feeding of the solution of the base is monitored by means of a measurement of the pH in the aqueous phase in the first reaction zone.

In the process according to the invention, a biphasic reaction mixture which has two liquid phases forms in the first reaction zone. The first, aqueous phase comprises the majority of the base used and of the chloride salt or carboxylate salt formed in the reaction with the base. The second, organic phase comprises the majority of the acyl compound used and of the acyl peroxide formed in the reaction.

In the process according to the invention, in the first reaction zone, the biphasic reaction mixture is maintained in a circulation which comprises a heat exchanger in which the reaction mixture is cooled. Preferably, in each pass through the circulation, the reaction mixture is passed completely or in part through the heat exchanger. More preferably, in each pass through the circulation, the entire reaction mixture is passed through the heat exchanger. In a particularly preferred embodiment, the first reaction zone used is a loop reactor in which the reaction mixture is conveyed through a heat exchanger with a pump.

The speed of the circulation in the first reaction zone is preferably selected so as to give rise to a circulation ratio of at least 2, preferably at least 5. For economic reasons, the circulation ratio is generally less than 1000, in particular less than 100. The circulation ratio represents the mass ratio of reaction mixture circulating in the first reaction zone to reaction mixture withdrawn from the first reaction zone.

Any heat exchanger known from the prior art which is suitable for cooling a biphasic liquid mixture may be used as the heat exchanger. Preferably, tube bundle heat exchangers or plate heat exchangers, in which the reaction mixture flows through the tubes or gaps between the plates, are used. The heat exchanger is preferably designed such that the reaction mixture is conveyed through channels or gaps of the heat exchanger which have a hydraulic diameter of less than 50 mm, more preferably less than 10 mm. The heat exchanger is preferably dimensioned such that the ratio between the cooling area of the heat exchanger and the volume of the first reaction zone is at least $1.5 \, m^2/m^3$ and more preferably at least $15 \, m^2/m^3$. Preferably, the design and dimensioning of the heat exchanger is chosen to establish a predominantly turbulent flow within the heat exchanger, which brings about dispersion by droplet disruption in the biphasic reaction mixture.

The addition of the acyl compound into the first reaction zone is effected preferably into the circulation of the first reaction zone, more preferably at a point at which the flow rate of the reaction mixture is more than 0.05 m/s, in particular more than 0.5 m/s.

In a preferred embodiment of the process according to the invention, the circulation in the first reaction zone also comprises a mixer which brings about dispersion through droplet disruption in the biphasic reaction mixture. In this embodiment, the acyl compound is added into the first reaction zone preferably immediately upstream of the mixer. Suitable mixers are all mixers which are known by those skilled in the art to be suitable for droplet disruption in biphasic liquid mixtures. Particularly suitable mixers are static mixers, for example static mixers of the Sulzer SMV or SMX mixer design. In another preferred embodiment, the mixer used is a circulation pump for the circulation in the first reaction zone, especially a centrifugal pump. In the case of suitable design and dimensioning, suitable mixers are also, as described above, the heat exchangers used in the process according to the invention.

In a further preferred embodiment of the process according to the invention, the reaction zones downstream of the first reaction zone are designed in the form of a stirred cell reactor. A stirred cell reactor has, within one casing, two or more reaction zones connected in series, each of the reaction zones being mixed by at least one stirrer and the stirrers being driven by a common motor, preferably by means of a common driving shaft. The reaction zones are connected to one another such that there is virtually no backmixing of the reaction mixture from one reaction zone into the upstream reaction zone. The reaction zones may, for example, be separate from one another and be connected to one another only via pipes. Alternatively, the reaction zones may also be connected to one another via sieve trays or valve trays which are dimensioned such that there is virtually no backmixing.

The reaction zones downstream of the first reaction zone may have cooling devices with which the heat of reaction released in these reaction zones is removed. The cooling devices used may, for example, be heat exchangers as in the first reaction zone. Alternatively, it is also possible to use reactors with a cooling jacket.

In the process according to the invention, an acyl compound from the group of the acid chlorides, carboxylic anhydrides and chloroformates is used.

The acid chloride used is preferably a compound from the group of acetyl chloride, propionyl chloride, butyryl chloride, isobutyryl chloride, valeroyl chloride, 2-methylbutyryl chloride, pivaloyl chloride, 2-methylpentanoyl chloride, 2-ethylbutyryl chloride, 2-ethylhexanoyl chloride, nonanoyl chloride, 2,4,4-tri-methylpentanoyl chloride, 3,5,5-trimethylhexanoyl chloride, decanoyl chloride, neodecanoyl chloride, lauroyl chloride, benzoyl chloride, 2-methylbenzoyl chloride, 4-methylbenzoyl chloride, 4-chlorobenzoyl chloride, 2,4-dichlorobenzoyl chloride and naphthoyl chloride. The acid chloride used is more preferably pivaloyl chloride, 2-ethylhexanoyl chloride or benzoyl chloride.

The carboxylic anhydride used is preferably a compound from the group of acetic anhydride, succinic anhydride, maleic anhydride and phthalic anhydride.

The chloroformate used is preferably a compound from the group of methyl chloroformate, ethyl chloroformate, n-propyl chloroformate, isopropyl chloroformate, n-butyl chloroformate, sec-butyl chloroformate, 2-ethylhexyl chloroformate, isotridecyl chloroformate, myristyl chloroformate, cetyl chloroformate, stearyl chloroformate, cyclohexyl chloroformate, 4-tert-butyl-cyclohexyl chloroformate, benzyl chloroformate and 2-phenoxyethyl chloroformate. Particular preference is given to using 2-ethylhexyl chloroformate as the chloroformate.

In the process according to the invention, a peroxygen compound from the group of the organic hydroperoxides and hydrogen peroxide is used.

The organic hydroperoxide used is preferably a compound from the group of tert-butyl hydroperoxide, tert-amyl hydroperoxide, 1,1,3,3-tetramethylbutyl hydroperoxide, 2,5-dimethylhexane 2,5-dihydroperoxide, 2,5-dimethyl-3-hexyne 2,5-dihydroperoxide, p-menthane hydroperoxide, pinane hydroperoxide, tetralin hydroperoxide, cumene hydroperoxide, 4-tert-butylcumene hydroperoxide, 1,3-diisopropylbenzene dihydroperoxide and 1,4-diiso-propylbenzene dihydroperoxide. Particular preference is given to using tert-butyl hydroperoxide as the organic hydroperoxide.

Acyl compounds and/or organic hydroperoxides which are solid under the reaction conditions used are preferably used in the form of a solution in a solvent. Suitable solvents are all solvents which are known to those skilled in the art and react under the reaction conditions neither with the acyl compound nor with the organic hydroperoxide or the base. Preference is given to using solvents which, at the reaction temperature used, have a solubility in water of less than 1 g/l. Suitable solvents are, for example, toluene and isododecane.

In the case of preparation of acyl peroxides which are solid under the reaction conditions used, preference is given to using a solvent for the acyl peroxide in an amount which, downstream of the last reaction zone, leads to a biphasic reaction mixture which, as the organic phase, has a liquid solution of the acyl peroxide in the solvent. Preference is given to using solvents which, at the reaction temperature used, have a solubility in water of less than 1 g/l. Suitable solvents are, for example, toluene and isododecane.

In the case of preparation of acyl peroxides which are liquid under the reaction conditions used, the reaction is preferably performed without solvent.

In the case of reaction of an acid chloride of the structure $R^1C(O)Cl$ or of a carboxylic anhydride of the structure $R^1C(O)OC(O)R^1$ with a hydroperoxide of the structure $R^2OOH$, a percarboxylic ester of the structure $R^1C(O)OOR^2$ is obtained in the process according to the invention. In this case, the acyl compound and the hydroperoxide are preferably used in a molar ratio of 1:0.8 to 1:2, more preferably 1:1 to 1:1.5. The molar ratio of acyl compounds to base (preferably as an alkali metal hydroxide) is preferably in the range of 1:0.8 to 1:5, more preferably 1:1 to 1:3.5. The base is preferably added so as to give rise to a pH in the range of 8 to 14, preferably 11 to 14, in the aqueous phase of the reaction mixture in the first reaction zone. The reaction is effected preferably at a temperature in the range of −10 to 50° C., more preferably 10 to 40° C.

In the case of reaction of an acid chloride of the structure $R^1C(O)Cl$ or of a carboxylic anhydride of the structure $R^1C(O)OC(O)R^1$ with hydrogen peroxide, the process according to the invention affords a diacyl peroxide of the structure $R^1C(O)OOC(O)R^1$. In this case, the acyl compound and hydrogen peroxide are used preferably in a molar ratio of 2:1 to 2:4, more preferably 2:1 to 2:1.5. The molar ratio of acyl compound to base (preferably as an alkali metal hydroxide) is preferably in the range of 1:1 to 1:2, more preferably 1:1 to 1:1.5. The base is preferably added so as to give rise to a pH in the range of 8 to 14, preferably 10 to 14, in the aqueous phase of the reaction mixture in the first reaction zone. The reaction is preferably effected at a temperature in the range of −10 to 50° C., more preferably 0 to 40° C.

In the case of reaction of a chloroformate of the structure $R^1OC(O)Cl$ with a hydroperoxide of the structure $R^2OOH$, the process according to the invention affords a peroxocarbonate of the structure $R^1OC(O)OOR^2$. In this case, the chloroformate and the hydroperoxide are used preferably in a molar ratio of 1:0.8 to 1:2, more preferably 1:1.2 to 1:1.5. The molar ratio of chloroformate to base (preferably as an alkali metal hydroxide) is preferably in the range of 1:0.8 to 1:2, more preferably 1:1.2 to 1:1.5. The base is preferably added so as to give rise to a pH in the range of 8 to 14, preferably 10 to 14, in the aqueous phase of the reaction mixture in the first reaction zone. The reaction is effected preferably at a temperature in the range of −10 to 50° C., more preferably 0 to 40° C.

In the case of reaction of a chloroformate of the structure $R^1OC(O)Cl$ with hydrogen peroxide, the process according to the invention affords a peroxodicarbonate of the structure $R^1OC(O)OOC(O)OR^1$. In this case, the chloroformate and hydrogen peroxide are used preferably in a molar ratio of 2:1 to 2:4, more preferably 2:1 to 2:1.5. The molar ratio of chloroformate to base (preferably as an alkali metal hydroxide) is preferably in the range of 1:1 to 1:2, more preferably 1:1 to 1:1.5. The base is preferably added so as to give rise to a pH in the range of 8 to 14, preferably 10 to 14, in the aqueous phase of the reaction mixture in the first reaction zone. The reaction is effected preferably at a temperature in the range of −10 to 50° C., more preferably 0 to 40° C.

The amounts of acyl compound, peroxygen compound and aqueous solution of base which are fed to the first reaction zone are preferably selected so as to achieve, in the first reaction zone, a conversion of acyl compound in the range of 60 to 99%, more preferably 85 to 95%.

A biphasic product mixture which comprises the produced acyl peroxide in the organic phase is withdrawn from the last reaction zone. This product mixture can be worked up further and purified by known processes. Preferably, the organic phase comprising the acyl peroxide is separated by a phase separation and then subjected to extraction with an alkaline aqueous solution in order to remove unconverted peroxygen compound and by-products formed in the reaction, for example carboxylic acid formed by hydrolysis of the acyl compound. The acyl peroxide can subsequently be subjected to further washes and drying, for which suitable processes are known to those skilled in the art from U.S. Pat. No. 4,075,236.

FIG. 1 shows a preferred embodiment of the process according to the invention, in which the reaction is effected in 6 reaction zones connected in series. The first reaction zone is designed as a loop reactor (1); the second to sixth reaction zones are designed as a stirred-cell reactor (2). The loop reactor (1) comprises a heat exchanger (3) in the form of a plate heat exchanger and a pump (4) in the form of a centrifugal pump which simultaneously also acts as a mixer for the biphasic reaction mixture. The peroxygen compound (5), an aqueous solution of a base (6) and the acyl compound (7) are fed to the loop reactor (1), the acyl compound being added immediately upstream of the pump (4) acting as the mixer. From the loop reactor (1), reaction mixture is fed to the stirred-cell reactor (2) via a connecting line (8). In the stirred-cell reactor (2), the reaction mixture passes from the bottom upward through 5 reaction zones (9), each of which is mixed by a stirrer (10), all stirrers being driven by a motor (11) by means of a common shaft. A biphasic product mixture (12) which comprises the produced acyl peroxide in the organic phase is withdrawn from the last reaction zone.

The process according to the invention allows for the preparation of acyl peroxides with improved space-time yields and higher product selectivities. The process can be performed safely even without solvent, since the reaction can be performed at temperatures below the self-accelerating decomposition temperature of the acyl peroxide, and the heat of reaction released in the reaction can be removed reliably. The process according to the invention allows the reactor volume required for a desired production capacity to be reduced, so that risks through operational disruption can be decreased.

The examples which follow illustrate the process according to the invention, but without restricting it.

EXAMPLES

Reactors Used

Reactor Type A:

Stirred cell reactor with 7 chambers of equal size arranged one on top of another with a common cooling jacket, which are separated from one another by 6 cooled plates and are connected to one another via passages between adjacent chambers. In each chamber, a stirrer is mounted, all stirrers being driven by means of a common shaft. The feedstocks or the reaction mixture of a preceding reactor are fed into the lowermost chamber. The converted reaction mixture is withdrawn by overflow from the uppermost chamber.

Reactor Type B:

Stirred cell reactor of the same design as reactor A, but three times the volume.

Reactor Type C:

Stirred cell reactor of the same design as reactor A, but with 6 chambers of volume 1.7 l each.

Reactor Type D:

Stirred tank with cooling jacket and internal cooling coils and 0.53 times the useful volume of reactor B.

Reactor Type E:

Loop reactor with a total volume of 2.2 l, consisting of a plate heat exchanger with a plate distance of 1 mm and a heat exchange area of 0.7 m², a circulation pump with a delivery output of 1 m³/h, and connecting lines between heat exchanger and circulation pump with an internal diameter of 14 mm. The feedstocks are fed into the connecting line immediately upstream of the circulation pump. The reactor has a ratio of cooling area of the heat exchanger to the volume of the reaction zone of 318 m²/m³. The flow rate at the addition point of the feedstocks is 1.8 m/s.

Example 1

Not Inventive

Preparation of tert-butyl peroxy-2-ethylhexanoate

The reaction is effected in a reactor arrangement of a first reactor of type A with a downstream reactor of type B. 2.42 kg/l·h of a 26% by weight solution of tert-butyl hydroperoxide and 17% by weight of potassium hydroxide in water and 0.86 kg/l·h of 2-ethylhexanoyl chloride are fed to the first reactor. The dosage rates are based on the total volume of the reactor arrangement in litres. Cooling with cooling water keeps the internal temperature in both reactors at 46° C. The reaction mixture withdrawn from the second reactor is mixed with 1.5 kg/l·h of demineralized water and the organic phase is removed. The organic phase is washed successively with an 8% by weight solution of sodium hydroxide in water, with a solution of 10% by weight of sodium sulphite in water comprising acetic acid, and with demineralized water, and then dried with calcium chloride. 1.06 kg/l·h of tert-butyl peroxy-2-ethylhexanoate are obtained (93.1% based on 2-ethyl-hexanoyl chloride).

Example 2

Inventive

Preparation of tert-butyl peroxy-2-ethylhexanoate

The reaction is effected in a reactor arrangement of a first reactor of type E with a downstream reactor of type C. Before the start of the reaction, the first reactor is filled with a solution of 25.8% by weight of tert-butyl hydroperoxide and 16.4% by weight of potassium hydroxide in water. 24.6 kg/h of a solution of 70% by weight of tert-butyl hydroperoxide in water, 24.2 kg/h of a solution of 45% by weight of potassium hydroxide in water, 17.4 kg/h of water and 24.0 kg/h of 2-ethylhexanoyl chloride are then fed to the first reactor. Cooling with cooling water keeps the internal temperature in the first reactor at 35° C. and in the second reactor at 27° C. The organic phase is removed from the reaction mixture withdrawn from the second reactor. The organic phase is washed successively with an 8% by weight solution of sodium hydroxide in water, with a solution of 10% by weight of sodium sulphite in water comprising acetic acid and with a 1% by weight solution of sodium hydrogencarbonate in water, and then dried by stripping in a column with random packing at 33° C. and 35 to 40 mbar. 31.4 kg/h of tert-butyl peroxy-2-ethylhexanoate are obtained (98.5% based on 2-ethylhexanoyl chloride). The space-time yield is 2.53 kg/l·h.

Example 3

Not Inventive

Preparation of tert-amyl peroxypivalate

The reaction is effected in a reactor arrangement of a first reactor of type D with two reactors of type B connected downstream in series. 0.26 kg/l·h of an 88% by weight solution of tert-amyl hydroperoxide in water, 0.47 kg/l·h of a 25% by weight solution of potassium hydroxide in water, 0.50 kg/l·h of a 25% by weight solution of sodium hydroxide in water and 0.26 kg/l·h of pivaloyl chloride are fed to the first reactor. The metering rates are based on the total volume of the reactor arrangement in litres. Cooling with cooling water keeps the internal temperature in the first reactor at 25° C. and in the two downstream reactors at 15° C. The reaction mixture withdrawn from the third reactor is mixed with 0.79 kg/l·h of demineralized water and 0.08 kg/l·h of isododecane, and the organic phase is removed. The organic phase is washed successively with an 8% by weight solution of sodium hydroxide in water, with a solution of 10% by weight of sodium sulphite in water comprising acetic acid and with demineralized, water, and then dried with calcium chloride. 0.42 kg/l·h of a 75% by weight solution of tert-amyl peroxypivalate in isododecane is obtained (80.6% based on pivaloyl chloride).

Example 4

Inventive

Preparation of tert-amyl peroxypivalate

The reaction is effected in a reactor arrangement of a first reactor of type E with a downstream reactor of type C. Before the start of the reaction, the first reactor is filled with a solution of 23.1% by weight of tert-amyl hydroperoxide, 9.9% by weight of potassium hydroxide and 8.3% by weight of sodium hydroxide in water. 20.2 kg/h of a solution of 88% by weight of tert-amyl hydroperoxide in water, 15.8 kg/h of a solution of 45% by weight of potassium hydroxide in water, 12.2 kg/h of a solution of 50% by weight of sodium hydroxide in water, 24.4 kg/h of water and 18.0 kg/h of pivaloyl chloride are then fed to the first reactor. Cooling with cooling water keeps the internal temperature in the first reactor at 18° C. and in the second reactor at 10° C. The reaction mixture withdrawn from the second reactor is mixed with 8.8 kg/h of isododecane and the organic phase is removed. The organic phase is washed successively with an 8% by weight solution of sodium hydroxide in water, with a solution of 10% by weight of sodium sulphite in water comprising acetic acid and with a 1% by weight solution of sodium hydrogencarbonate in water, and then dried by stripping in a packed column at 20° C. and 45 mbar. 35.0 kg/h of a 75% by weight solution of tert-amyl peroxypivalate in isododecane are obtained (93.5% based on pivaloyl chloride). The space-time yield is 2.82 kg/l·h.

Example 5

Not Inventive

Preparation of tert-butyl peroxy-3,5,5-trimethyl-hexanoate

The reaction is effected in a reactor arrangement of a first reactor of type A with a downstream reactor of type B. 2.25 kg/l·h of a 26% by weight solution of tert-butyl hydroperoxide and 17% by weight of potassium hydroxide in water and 0.75 kg/l·h of 3,5,5-trimethylhexanoyl chloride are fed to the first reactor. The metering rates are based on the total volume of the reactor arrangement in litres. Cooling with cooling water keeps the internal temperature in both reactors at 46° C. The reaction mixture withdrawn from the second reactor is mixed with 1.5 kg/l·h of demineralized water and the organic phase is removed. The organic phase is washed successively with an 8% by weight solution of sodium hydroxide in water, with a solution of 10% by weight of sodium sulphite in water comprising acetic acid and with demineralized water, and then dried with calcium chloride. 0.90 kg/l·h of tert-butyl peroxy-3,5,5-trimethylhexanoate is obtained (91.6% based on 3,5,5-trimethylhexanoyl chloride).

Example 6

Inventive

Preparation of tert-butyl peroxy-3,5,5-trimethyl-hexanoate

The reaction is effected in a reactor arrangement of a first reactor of type E with a downstream reactor of type C. Before the start of the reaction, the first reactor is filled with a solution of 25.6% by weight of tert-butyl hydroperoxide and 15.0% by weight of potassium hydroxide in water. 20.2 kg/h of a solution of 70% by weight of tert-butyl hydroperoxide in water, 18.2 kg/h of a solution of 45% by weight of potassium hydroxide in water, 16.2 kg/h of water and 19.2 kg/h of 3,5,5-trimethylhexanoyl chloride are then fed to the first reactor. Cooling with cooling water keeps the internal temperature in the first reactor at 25° C. and in the second reactor at 25° C. The organic phase is removed from the reaction mixture withdrawn from the second reactor. The organic phase is washed successively with an 8% by weight solution of sodium hydroxide in water, with a solution of 10% by weight of sodium sulphite in water comprising acetic acid and with a 1% by weight solution of sodium hydrogen-carbonate in water, and then dried by stripping in a packed column at 34° C. and 47 mbar. 24.6 kg/h of tert-butyl peroxy-3,5,5-trimethylhexanoate are obtained (98.2% based on 3,5,5-trimethylhexanoyl chloride). The space-time yield is 1.98 kg/l·h.

Example 7

Not Inventive

Preparation of tert-butyl peroxyisobutyrate

The reaction is effected in a reactor arrangement of a first reactor of type D with two reactors of type B connected downstream in series. 1.22 kg/l·h of a 26% by weight solution of tert-butyl hydroperoxide and 17% by weight of potassium hydroxide in water and 0.32 kg/l·h of isobutyroyl chloride are fed to the first reactor. The metering rates are based on the total volume of the reactor arrangement in litres. Cooling with cooling water keeps the internal temperature in the first reactor at 26° C. and in the two downstream reactors at 20° C. The reaction mixture withdrawn from the third reactor is mixed with 0.79 kg/l·h of demineralized water and 0.14 kg/l·h of isododecane, and the organic phase is removed. The organic phase is washed successively with an 8% by weight solution of sodium hydroxide in water, with a solution of 10% by weight of sodium sulphite in water comprising acetic acid and with demineralized water, and then dried with calcium chloride. 0.54 kg/l·h of a 75% by weight solution of tert-butyl peroxyisobutyrate in isododecane is obtained (86.0% based on isobutyroyl chloride).

Example 8

Inventive

Preparation of tert-butyl peroxyisobutyrate

The reaction is effected in a reactor arrangement of a first reactor of type E with a downstream reactor of type C. Before the start of the reaction, the first reactor is filled with a solution of 24.4% by weight of tert-butyl hydroperoxide and 12.7% by weight of potassium hydroxide in water. 33.6 kg/h of a solution of 70% by weight of tert-butyl hydroperoxide in water, 27.2 kg/h of a solution of 45% by weight of potassium hydroxide in water, 38.0 kg/h of water and 18.4 kg/h of isobutyroyl chloride are then fed to the first reactor. Cooling with cooling water keeps the internal temperature in the first reactor at 11° C. and in the second reactor at 12° C. The reaction mixture withdrawn from the second reactor is mixed with 8.0 kg/h of isododecane and the organic phase is removed. The organic phase is washed successively with an 8% by weight solution of sodium hydroxide in water, with a solution of 10% by weight of sodium sulphite in water comprising acetic acid and with a 1% by weight solution of sodium hydrogencarbonate in water, and then dried by stripping in a packed column at 20° C. and 47 mbar. 33.4 kg/h of a 75% by weight solution of tert-butyl peroxyisobutyrate in isododecane are obtained (92.8% based on isobutyroyl chloride). The space-time yield is 2.69 kg/l·h.

Example 9

Not Inventive

Preparation of tert-butyl peroxybenzoate

The reaction is effected in a reactor arrangement of a first reactor of type D with two reactors of type B connected downstream in series. 1.72 kg/l·h of a 19.5% by weight solution of tert-butyl hydroperoxide and 9.5% by weight of sodium hydroxide in water and 0.49 kg/l·h of benzoyl chloride are fed to the first reactor. The metering rates are based on the total volume of the reactor arrangement in litres. Cooling with cooling water keeps the internal temperature in all reactors at 25° C. The organic phase is removed from the reaction mixture withdrawn from the third reactor, washed successively with an 8% by weight solution of sodium hydroxide in water, with a solution of 10% by weight of sodium sulphite in water comprising acetic acid and with demineralized water, and then dried with calcium chloride. 0.61 kg/l·h of tert-butyl peroxybenzoate is obtained (89.9% based on benzoyl chloride).

Example 10

Inventive

Preparation of tert-butyl peroxybenzoate

The reaction is effected in a reactor arrangement of a first reactor of type E with a downstream reactor of type C. Before the start of the reaction, the first reactor is filled with a solution of 19.4% by weight of tert-butyl hydroperoxide and 8.9% by weight of sodium hydroxide in water. 18.4 kg/h of a solution of 70% by weight of tert-butyl hydroperoxide in water, 11.8 kg/h of a solution of 50% by weight of sodium hydroxide in water, 35.8 kg/h of water and 18.0 kg/h of benzoyl chloride are then fed to the first reactor. Cooling with cooling water keeps the internal temperature in the first reactor at 12° C. and in the second reactor at 11° C. The organic phase is removed from the reaction mixture withdrawn from the second reactor. The organic phase is washed successively with an 8% by weight solution of sodium hydroxide in water, with a solution of 10% by weight of sodium sulphite in water comprising acetic acid and with a 1% by weight solution of sodium hydrogencarbonate in water, and then dried by stripping in a packed column at 35° C. and 42 to 44 mbar. 33.8 kg/h of tert-tert-butyl peroxybenzoate are obtained (95.3% based on benzoyl chloride). The space-time yield is 2.73 kg/l·h.

The invention claimed is:

1. A continuous process for preparing an acyl peroxide comprising: feeding an acyl compound, a peroxygen compound and an aqueous solution of a base to a first mixed reaction zone, wherein said acyl compound is selected from the group consisting of an acid chloride, a carboxylic anhydride and a chloroformate, and said peroxygen compound is selected from the group consisting of an organic hydroperoxide and a hydrogen peroxide; to form a biphasic reaction mixture; wherein said first mixed reaction zone is connected in series to a second mixed reaction zone, wherein said first mixed reaction zone contains a heat exchanger through which said biphasic reaction mixture is circulated and cooled and wherein said first mixed reaction zone is a loop reactor.

2. The continuous process of claim 1, further comprising withdrawing circulating reaction mixture from said first mixed reaction zone wherein the ratio of remaining circulating reaction mixture to said withdrawn reaction mixture is at least 2.

3. The continuous process of claim 1, further comprising withdrawing circulating reaction mixture from said first mixed reaction zone wherein the ratio of remaining circulating reaction mixture to said withdrawn reaction mixture is at least 5.

4. The continuous process of claim 1, wherein said heat exchanger comprises a cooling area and the ratio between said cooling area and the first mixed reaction zone is at least 1.5 m2/m3.

5. The continuous process of claim 1, wherein the reaction mixture is conveyed through said heat exchanger with a pump.

6. The continuous process of claim 5, comprising conveying said reaction mixture through a pluralities of channels or gaps of said heat exchanger, said channels or gaps having a hydraulic diameter of less than 50 mm.

7. The continuous process of claim 1, wherein said first mixed reaction zone comprises a mixer and said acyl compound is added upstream of said mixer.

8. The continuous process of claim 1, comprising adding said acyl compound into the first mixed reaction zone at a flow rate more than 0.5 m/s.

9. The continuous process of claim 1, wherein the acyl peroxide is a liquid and the circulating process is carried out without addition of a solvent.

10. The continuous process of claim 1, wherein said continuous process is carried out in more than two mixed reaction zones connected in series, and the second and all following reaction zones are stirred cell reactors.

11. The continuous process of claim 1, wherein the acyl compound is an acid chloride selected from the group consisting of an acetyl chloride, a propionyl chloride, a butyryl chloride, an isobutyryl chloride, a valeroyl chloride, a 2-methylbutyryl chloride, a pivaloyl chloride, a 2-methylpentanoyl chloride, a 2-ethylbutyryl chloride, a 2-ethylhexanoyl chloride, a nonanoyl chloride, a 2,4,4-trimethylpentanoyl chloride, a 3,5,5-trimethylhexanoyl chloride, a decanoyl chloride, a neodecanoyl chloride, a lauroyl chloride, a benzoyl chloride, a 2-methylbenzoyl chloride, a 4-methylbenzoyl chloride, a 4-chlorobenzoyl chloride, a 2,4-dichlorobenzoyl chloride and a naphthoyl chloride.

12. The continuous process of claim 1, wherein the acyl compound is a chloroformate selected from the group consisting of a methyl chloroformate, an ethyl chloroformate, a n-propyl chloroformate, an isopropyl chloroformate, a n-butyl chloroformate, a sec-butyl chloroformate, a 2-ethylhexyl chloroformate, an isotridecyl chloroformate, a myristyl chloroformate, a cetyl chloroformate, a stearyl chloroformate, a cyclohexyl chloroformate, a 4-tert-butylcyclohexyl chloroformate, a benzyl chloroformate and a 2-phenoxy-ethyl chloroformate.

13. The continuous process of claim 1, wherein the peroxygen compound is an organic hydroperoxide selected from the group consisting of a tert-butyl hydroperoxide, a tert-amyl hydroperoxide, a 1,1,3,3-tetramethylbutyl hydroperoxide, a 2,5-dimethylhexane 2,5-dihydroperoxide, a 2,5-dimethyl-3-hexyne 2,5-dihydroperoxide, a p-menthane hydroperoxide, a pinane hydroperoxide, a tetralin hydroperoxide, a cumene hydroperoxide, a 4-tert-butylcumene hydroperoxide, a 1,3-diisopropylbenzene dihydroperoxide and a 1,4-diisopropylbenzene dihydroperoxide.

* * * * *